United States Patent [19]

Paul et al.

[11] Patent Number: 5,419,907
[45] Date of Patent: May 30, 1995

[54] PATHOGENIC PORCINE RESPIRATORY CORONAVIRUS

[75] Inventors: Prem S. Paul; Eric M. Vaughn; Patrick G. Halbur, all of Ames, Iowa

[73] Assignee: Iowa State University Research Foundation, Inc., Ames, Iowa

[21] Appl. No.: 974,251

[22] Filed: Nov. 10, 1992

[51] Int. Cl.⁶ ............... A61K 39/215; A61K 39/225; C12N 7/06; C12N 7/08
[52] U.S. Cl. ............... 424/221.1; 424/223.1; 424/815; 435/237; 435/238
[58] Field of Search ............. 424/88, 89, 221.1, 223.1, 424/815; 435/239, 236, 237, 238

[56] References Cited

PUBLICATIONS

Proc. Conf. Ref. Workers Anim. Dis., Abstract No. 213, 1991, p. 38, Vaughn et al., "Characterization and Pathogenicity of Porcine Respiratory Coronavirus AR310 Isolated From a Swine Herd with Transmissible Gastroenteritis".
Proc. Int. Pig Vet. Soc. Congn., vol. 12, 1992, p. 92, Paul et al., "Characterization and Pathogenicity of a New Porcine Respiratory Coronavirus Strain AR310".
Journal of Veterinary Diagnostic Investigatigaton, vol. 5, No. 2, Apr. 1993, Colombia, Mo., pp. 184–188, Halbur et al., "Experimental Reproduction of Pneumonia in Gnotobiotic Pigs with Porcine Respiratory Coronavirus Isolate AR31".
Callebaut et al: Adv Exp Med Biol 276: 421–428, 1990.
Bernard et al; Vet Microbiol 21(1): 1–8, 1989.
Paton et al; Vet Res Commun 14(4):329–337, 1990.
Callebaut et al; J Gen Virol 69(7):1725–1730, 1988.
Van Nieuwstadt et al. Am J Vet Res 52(2):184–190, 1992.
M. B. Pensaert, "Transmissible Gastroenteritis Virus (Respiratory Variant)", in *Coronaviruses*, S. G. Siddell, E. D., pp. 154–165, Plenum, New York, (1992).
C. M. Sanchez, et al., in *Virology*, 190, 92 (1992).
R. D. Wesley, et al., *J. Vet. Diagn. Invest.*, 3:29–32 (1991).
R. D. Wesley, et al., *J. Virol.*, 65, 3369 (1991).
D. Rasschaert et al., *J. Gen Virol.*, 71, 2599 (1990).
C. M. Sanchez, et al., *Virology*, 174, 410 (1990).
R. D. Wesley, et al., *J. Vet. Diag. Invest.*, 2, 312 (1990).
X. Zhu, et al., *Am. J. Vet. Res.*, 51, 232 (1990).
P. Callebaut, et al., *Veterinary*, 20:9–19 (1989).
H. T. Hill et al., *Proc. Am. Assoc. Swine Prac.*, pp. 333–334 (1989).
M. B. Pensaert, et al., *Agri-Practice*, 10(2):17–21, Mar.-/Apr. (1989).
D. O'Toule et al., *Res. Vet. Sci.*, 47, 23 (1989).
A. P. Van Nieuwstadt et al., *Veterinary Record*, 124, 43 (1989).
P. Callebaut, et al., *J. Gen. Virol.*, 69, 1725 (1988).
C. Duret et al., *Recueil de Medecine Veterinaire*, 164, 221–226 (1988).
J. Garwes, et al., *Veterinary Record*, 122, 86 (1988).
H. Laude et al., *Journees de law Recherche Porcine en France*, 20, 89 (1988).
A. Jestin et al., *Recueil de Medecine Veterinaire*, 163, 567–571 (1987).
M. Pensaert, et al., *Veterinary Quaterly*, 8, 257 (1986).
O. P. Miniats et al., *Can. J. Comp. Med.*, 42, 428 (1978).
H. W. Moon, *J. Am. Vet. Med. Assoc.*, 172, 332 (1978).
L. J. Kemeny, et al., *Cornell Vet.*, 65, 352 (1975).
Kohler, et al., *Nature*, 256, 495–97 (1975).

*Primary Examiner*—Christine M. Nucker
*Assistant Examiner*—Julie Krsek-Staples
*Attorney, Agent, or Firm*—Schwegman, Lundberg & Woessner

[57] ABSTRACT

The present invention provides a biologically pure culture of a novel pathogenic porcine respiratory coronavirus (PRCV) and a vaccine derived therefrom effective against PRCV infection and transmissible gastroenteritis virus (TGEV) infection.

6 Claims, 2 Drawing Sheets

```
                    10         20         30         40         50         60         70
310-1-9   GAATTCGGGTAAGTTGCTCATTAGAAATAATGGTAAGTTACTAAACTTTGGTAACCACTTCGTTAATGCA
310-1-10  .....................................................G..........A..

80         90        100        110        120        130        140
         [S Start]
310-1-9   CCATGAAACATTATTGTGGTTTTGGTTATAATGCCATTGATTATGGAGACCTTTGGTGGTTTAATCC
310-1-10  ..............C...................................  ← +621 nucleotides unique to TGEV
```

Fig. 1

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 140 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

```
GAATTCGGGT AAGTTGCTCA TTAGAAATAA TGGTAAGTTA CTAAACTTTG GTAACCACTT        60

CGTTAATGCA CCATGAAAAC ATTATTTGTG GTTTTGGTTA TAATGCCATT GATTTATGGA       120

GACCTTTGGT GGTTTAATCC                                                   140
```

( 2 ) INFORMATION FOR SEQ ID NO:2:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:2:

```
ATGAAAAAAT TATTTGTGGT TTTGGTTGTA ATGCCATTGA TTTATGGAGA CAATTTTCC         60

TGTTCTAAAT                                                              70
```

( 2 ) INFORMATION FOR SEQ ID NO:3:

( i ) SEQUENCE CHARACTERISTICS:
        ( A ) LENGTH: 29 base pairs
        ( B ) TYPE: nucleic acid
        ( C ) STRANDEDNESS: single (D) TOPOLOGY: linear (ii) MOLECULE TYPE: DNA (genomic)

(xi) SEQUENCE DESCRIPTION: SEQ ID NO:3:

GGGGATCCGG ACCTGTAATG ACTCGTAAG    29

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:4:

GGGAATTCGG GTAAGTTGCT CATTAGAAA    29

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:5:

GGGGATCCGC AGTGCCACGA GTCCTATCAT    30

PATHOGENIC PORCINE RESPIRATORY CORONAVIRUS

BACKGROUND OF THE INVENTION

Transmissible gastroenteritis virus (TGEV) causes a fatal diarrheal disease in neonatal piglets because it selectively infects and destroys the small-intestinal enterocytes required for nutrient absorption and fluid regulation (H. W. Moon, *J. Am. Vet. Med. Assoc.*, 172, 443 (1978)). Additionally, TGEV replicates in porcine respiratory tract tissues but this does not result in primary respiratory disease (L. J. Kemeny et al., *Cornell Vet.*, 65, 352 (1975)).

A new porcine respiratory coronavirus, tentatively designated PRCV, which has a close antigenic relationship to TGEV, suddenly emerged in 1983 to 1984 and spread within less than 2 years in most if not all European countries, where it now persists enzootically. A cytopathic agent has been isolated in cell culture and pathogenesis studies have shown that it replicated at a high titre in the respiratory tract, but to a very low extent in the gut (M. Pensaert et al., *Veterinary Quarterly*, 8, 257 (1986)).

Conventional serological tests do not distinguish between PRCV- and TGEV-infected animals. However, antigenic dissimilarities were evident on examining the heterologous reactivity of monoclonal antibodies (MAbs). PRCV was found to be non-reactive towards several non-neutralizing anti-TGEV MAbs directed against the S (spike) or M (membrane) proteins (P. Callebaut et al., *J. Gen. Virol.*, 69, 1725 (1988); J. Garwes et al., *Veterinary Record*, 122, 86 (1988)). Neutralization-mediating epitopes unique to TGEV have been identified also, e.g., by H. Laude et al., *Journees de la Recherche Porcine en France*, 20, 89 (1988). Conversely, anti-PRCV S-specific MAbs have been shown to differentiate between the two viruses.

Both types of viruses have common antigenic determinants in the three structural proteins: spike (S), membrane (M), and nucleoprotein (N). The absence of two antigenic sites in the S protein of the PRCV isolates has been the base for their differentiation from the enteric viruses by C. M. Sánchez et al., *Virology*, 174, 410 (1990). Sequencing of the S gene of a French PRCV isolate by D. Rasschaert et al., *J. Gen. Virol.*, 71, 2599 (1990), and of a 200-nucleotide (nt) fragment of the S gene of a North American PRCV isolate by R. D. Wesley et al., *J. Virol.*, 65, 3369 (1991) has revealed that both S proteins contain, at comparable locations within the protein, a single deletion of 224 and 227 amino acids, respectively.

More recently, C. M. Sánchez et al., in *Virology*, 190, 92 (1992) determined the genetic relationship among six European PRCVs and five coronaviruses of the TGEV antigenic cluster, based upon their RNA sequences. The S proteins of the six PRCVs were found to have an identical deletion of 224 amino acids starting at position 21. The deleted area includes the antigenic sites C and B of the TGEV S glycoprotein.

The significance of this virus as a pathogen is still unclear. Although it was first considered as non-pathogenic, subsequent investigations by A. Jestin et al., *Recueil de Medecine Veterinaire*, 163, 567 (1987); C. Duret et al., ibid., 164, 221 (1988); D. O'Toule et al., *Res. Vet. Sci.*, 47, 23 (1989) and A. P. Van Nieuwstadt et al., *Veterinary Record*, 124, 43 (1989) have linked PRCV with field outbreaks of respiratory disease and with pneumonic lesions following an experimental infection.

Porcine respiratory coronavirus was first isolated in the United States in 1989. This isolate was designated as ISU-1-PRCV or Ind-89. Subsequently, ISU-2-PRCV was isolated from a herd in North Carolina. The herds involved seroconverted to TGEV without showing clinical signs of respiratory or enteric disease. See, H. T. Hill et al., *Proc. Am. Assoc. Swine Prac.*, p. 333–335, (1989). ISU-1-PRVC replicated in the lungs of experimentally inoculated neonatal pigs but did not cause significant respiratory lesions. See, R. D. Wesley et al., *J. Vet. Diag. Invest.*, 2, 312 (1990).

Therefore, a need exists for the isolation and characterization of novel pathogenic strains of TGEV, particularly with respect to pathogenic strains which may have evolved in the United States. Since it has been proposed by L. Enjuanes et al, in *Coronaviruses*, S. G. Siddell, ed., Plenum, N.Y. (1992) that PRCV behaves as a natural vaccine against TGEV, such PRCV strains could provide the basis for vaccines against both TGEV and pathogenic PRCV.

SUMMARY OF THE INVENTION

The present invention provides biologically pure culture of a novel TGEV-related porcine respiratory corona-virus (PRCV) strain, designated AR310 and zoopathogenic mutants thereof. A sample of this strain has been deposited on Nov. 6, 1992 under the terms of the Budapest Treaty in the American Type Culture Collection, Parklawn Drive, Rockville, Md. 20852 USA under the designation ATCC VR 2384. AR310 was isolated from intestinal tissue of a piglet from a domestic (U.S.) swine herd afflicted with endemic transmissible gastroenteritis (TGE). The PRCV isolate AR310 was readily neutralized by anti-transmissible gastroenteritis virus (TGEV) polyclonal swine sera and by neutralizing monoclonal antibodies directed against the S glycoprotein of TGEV.

Analysis of the $^{35}$S-methionine-cysteine labeled S glycoprotein by radioimmunoprecipitation revealed a truncated S glycoprotein with a $M_r$ of about 181,000 as compared to the expected $M_r$ of 200,000 for TGEV. The 5' half of the S gene cDNA of PRCV AR310 was amplified by the polymerase chain reaction (PCR), cloned, and was partially sequenced. Analysis of the 5' half of the S gene showed that a 621 bp deletion is present. This 621 bp deletion in the 5' end of PRCV AR310 differs from that present in other PRCV isolates in that it is shorter than those of previously published PRCV S gene deletions and also differs in that the 621 bp deletion occurs closer to the signal peptide region of the S gene than other published PRCV S gene sequences.

Eight gnotobiotic pigs were inoculated intranasally with $2\times 10^6$ PFU of AR310 which had been passaged once in gnotobiotic pigs. Eight pigs inoculated with cell culture medium served as mock-infected controls. Two pigs from each group were necropsied at 3, 5, 10 and 15 days post-infection (DPI). Mild patchy broncho-interstitial pneumonia was observed starting at day 3 after infection. The lung lesions progressed and were severe and diffuse by day 10. By day 15, the lung lesions appeared to be resolving. All control pigs remained normal throughout the study and had no visible gross or microscopic lesions. Neither virus replication nor microscopic lesions were evident in the small intestines of the inoculated pigs. These studies show that isolate AR310 is a PRCV and is capable of producing significant pneumonic lesions in gnotobiotic pigs.

Thus, the present invention also provides a vaccine comprising an amount of inactivated viral isolate AR310 or a zoopathogenic mutant thereof, which is effective to immunize susceptible pigs against infection by PRCV and/or TGEV, wherein said amount is preferably suspended in a physiologically acceptable injectable liquid vehicle, in combination with an immunological adjuvant or adjuvants. The present invention also provides a method to vaccinate susceptible swine against PRCV or TGEV by employing an immunologically effective amount of said vaccine.

Antigenic polypeptides derived from AR310, such as the S glycoprotein, are also within the scope of the present invention, as are polyclonal and monoclonal antibodies which specifically bind to AR310 or subunit antigenic polypeptides derived therefrom. Also provided by the present invention are methods to employ these antibodies for the detection of pathogenic PRCV.

A diagnostic method for swine PRCV infection is also provided, which can discriminate between TGEV and PRCV infection. The assay comprises (a) contacting a sample of a swine physiological material, such as a fluid containing antibodies which specifically bind to AR310 with a sample of AR310 or an antigenic polypeptide derived therefrom, which sample has preferably been immobilized on a solid substrate, so that said antibodies bind to said AR310 or to the AR310-derived polypeptides, and (b) detecting the presence of said bound antibodies.

DETAILED DESCRIPTION OF THE INVENTION

The vaccine can comprise an inactivated or attenuated AR310, derived from an inoculum processed from infected swine lung tissue or other swine tissue exhibiting the characteristic lesions of pathological PRCV, as described below. Immunogenic derivatives of AR310, including subunit, vector, recombinant, and synthetic peptide vaccines, or the like, are also envisioned.

A multi-step procedure can be utilized in developing the PRCV vaccine. Lung or other swine tissue from TGEV-infected, asymptomatic pigs is homogenized with a pharmaceutically acceptable aqueous solution (such as physiological saline, Ringers solution, Hank's Balanced Salt Solution, Minimum Essential Medium, and the like) such that the tissue comprises 10 percent weight/volume amount of the homogenate. The homogenate is then centrifuged and passed through filters with pore diameters in the 0.05 to 10 micron range, to produce a filtered homogenate containing the AR310 viral infectious agent. The filtered homogenate can then be mixed with Freund's incomplete adjuvant so that the production of antibodies can be stimulated upon injection of the homogenate into a mammal. This mixture can be used as an inoculum for development of pathological PRCV in swine or further study of AR310.

To produce a purified form of the infectious agent, the filtered homogenate described above can be inoculated into in vitro cell preparations. Cell preparations with mammalian organ cells such as kidney, liver, heart and brain, lung, spleen, testicle, turbinate, white and red blood cells and lymph node, as well as insect and avian embryo preparations can be used. Culture media suitable for these cell preparations include those supporting mammalian cell growth such as fetal calf serum and agar, blood infusion agar, brain-heart infusion glucose broth and agar and the like. Preferably, the mammalian cells are swine testis cells. Purified viral particles can be isolated from clarified cell supernatant fluids by precipitation and centrifugation in accord with standard protocols.

After inoculating the cell preparation with the filtered homogenate and growing the viral culture, individual clumps of cultured cells are harvested and reintroduced into sterile culture medium with fresh cells. The culture fluid from the final culture of the series provides the purified form of the virulent infectious agent. Also, after a series of repeated harvests have been made, the culture can be grown, the culture fluid collected and the fluid used as an inoculum for a culture of a different cellular species. In this fashion, the infective agent can be attenuated so that the culture fluid from the differing species culture provides the purified form of the attenuated infectious agent.

To prepare a vaccine against pathological PRCV, viral strain AR310 can be inactivated or killed by treatment of the filtered homogenate comprising the virus with a standard chemical inactivating agent, such as an aldehyde reagent including formalin, acetaldehyde and the like; reactive acidic alcohols including cresol, phenol and the like; acids such as benzoic acid, benzene sulfonic acid and the like; lactones such as beta propiolactone and caprolactone; and activated lactams, carbodiimides and carbonyl diheteroaromatic compounds such as carbonyl diimidazole. Irradiation such as with ultraviolet and gamma irradiation can also be used to inactivate or kill the virus. Alternatively, the virus can be attenuated by its repeated growth in cell culture from non-swine mammal or avian origin so that the ability of the infectious agent to virulently reproduce is lost.

The killed or attenuated infectious agent is then diluted to an appropriate titer by addition of a diluent/adjuvant solution for stimulation of immune response. The titration is accomplished by measurement against a PRCV or TGE antibody in an immunologic test such as an ELISA, RIA, IFA or enzyme substrate detection test.

The vaccine of the present invention is capable of preventing and curing PRCV and/or TGEV infections found in the swine population. For effective prophylactic and anti-infectious use in vivo, the vaccine contains killed or attenuated strain AR310 and may be administered alone or in combination with a pharmaceutical carrier that is compatible with swine. The vaccine may be delivered orally, parenterally, intranasally or intravenously. Factors bearing on the vaccine dosage include, for example, the age, weight, and level of maternal antibody of the infected pig. The range of a given dose is $10^3$ to $10^7$ Tissue Culture Infective Dose 50 per ml, preferably given in 1 ml to 5 ml doses. The vaccine doses should be applied over about 14 to 28 days to ensure that the pig has developed an immunity to the PRCV and/or TGEV infection.

The vaccine can be administered in a variety of different dosage forms. An aqueous medium containing the killed or attenuated AR310 may be desiccated and combined with pharmaceutically acceptable inert excipients and buffering agents such as lactose, starch, calcium carbonate and sodium citrate formed into tablets, capsules and the like. These combinations may also be formed into a powder or suspended in an aqueous solution such that these powders and/or solutions can be added to animal feed or to the animals' drinking water. These vaccine powders or solutions can be suitably sweetened or flavored by various known agents to promote the uptake of the vaccine orally by the pig.

For purposes of parenteral administration, the killed or attenuated AR310 can be combined with pharmaceutically acceptable carrier(s) well known in the art such as saline solution, water, propylene glycol, triacetin, and the like. In this form, the vaccine can be parenterally, intranasally, and orally administered by methods known to the art of veterinary medicine. The vaccine can also be administered intravenously by syringe. In this form, the vaccine is combined with pharmaceutically acceptable aqueous carrier(s) such as a saline solution. The parenteral and intravenous formulations of vaccine may also include emulsifying and/or suspending agents as well, together with pharmaceutically acceptable diluent to control the delivery and the dose amount of the vaccine.

To prepare a vaccine, the inactivated virus can be isolated, lyophilized, stabilized, and clan be adjusted to an appropriate concentration with a physiologically acceptable liquid vehicle such as normal saline, phosphate-buffered saline, and the like, optionally combined with a suitable vaccine adjuvant, and packaged for use. Suitable adjuvants include but are not limited to: surfactants, e.g., hexadecylamine, octadecylamine, lysolecithin, dimethyldioctadecylammonium bromide, N,N-dioctadecyl-N'-N-bis(2-hydroxyethyl-propane diamine), methoxyhexadecylglycerol, and pluronic polyols; polanions, e.g., pyran, dextran sulfate, poly IC, polyacrylic acid, carbopol; peptides, e.g., muramyl dipeptide, dimethylglycine, tuftsin, oil emulsions, alum, and mixtures thereof. Finally, the immunogenic product may be incorporated into liposomes for use in a vaccine formulation, or may be conjugated to albumin, polysaccharides or other polymers.

The absolute weight of the polypeptide included in a given unit dosage form of vaccine can vary widely, e.g., from about 5 $\mu$g-300 mg, and will depend upon factors such as the age, weight and physical condition of the pig considered for vaccination. Such factors can be readily determined by the clinician or veterinarian employing animal models or other test systems which are well known to the art. A unit dose of the vaccine is preferably administered parenterally, e.g., by subcutaneous or by intramuscular injection.

Polyclonal antibody sera can be produced through use of AR310 as an antigenic substance to raise an immune response in mammals. The culture fluid or inoculum comprising AR310 can be administered with a stimulating adjuvant to a non-swine mammal such as a horse, goat, mouse or rabbit. After repeated challenge, portions of blood serum can be removed and antigenically purified using immobilized antibodies to those disease-specific antibodies typically found in the serum of the bled animal. Further treatment of the semi-purified serum by chromatography on, for example, a saccharide gel column with physiological saline and collection of proteinaceous components of molecular weight at least 10,000 provides a purified polyclonal sera for use in treatment.

Monoclonal antibody sera can be produced by the hybridoma technique. After immunization of a mouse, pig, rat, rabbit or other appropriate species with AR310 containing cell culture lysate or gradient-purified AR310 as described above, the spleen of the animal can be removed and converted into a whole cell preparation. Following the method of Kohler and Milstein (Kohler et al, *Nature*, 256, 495–97 (1975)), the immune cells from the spleen cell preparation can be fused with myeloma cells to produce hybridomas. Culturation of the hybridomas and testing the culture fluid against the fluid or inoculum carrying the infectious agent allows isolation of the hybridoma culture producing monoclonal antibodies to the infectious agent. Introduction of the hybridoma into the peritoneum of the host species will produce a peritoneal growth of the hybridoma. The ascites fluid then provides a source of the monoclonal antibody to the infectious agent. Also, cell culture supernatant from the hybridoma cell culture can be used. Preferably, the monoclonal antibody is produced by a murine-derived hybrid cell line wherein the antibody is an IgG or IgM type immunoglobulin. Monoclonal antibodies can be employed in various diagnostic and therapeutic compositions and methods, including passive immunization and anti-idiotype vaccine preparation.

The method for diagnosis of pathological PRCV is carried out with the polyclonal or monoclonal antibody sera described above. Either the antibody sera or the biopsied tissue homogenate may be immobilized by contact with a polystyrene surface or with a surface of another polymer for immobilizing protein. The other of the antibody sera and homogenate is then added, incubated and the non-immobilized material removed, for example, by washing. A labeled species-specific antibody for the antibody sera is then added and the presence and quantity of label determined. The label determination indicates the presence of AR310 in the tissue assayed. Typical embodiments of this method include the enzyme-linked immunosorbent assay (ELISA); radioimmunoassay (RIA); immunofluorescent assay (IFA); and Western Blot immunoassay.

The invention will be further described by reference to the following detailed examples wherein the Miller (American Type Culture Collection, Rockville, Md.) strain of TGEV was used as a standard TGEV strain in this study. The PRCV isolate ISU-1 was kindly provided by Dr. Howard Hill (Iowa State University Veterinary Diagnostic Laboratory).

The RM4, PRCV 86/137004, and Ind/89 PRCV isolates were isolated from swine herds with mild respiratory disease that had high titers to TGEV yet had not presented any signs of enteric disease accompanied with TGEV infection.

Example 1. Virus Isolation

Small intestines of pigs from a swine herd in Arkansas (for isolates AR302 and AR310) or a swine herd from Iowa (for isolate IA101) with transmissible gastroenteritis were obtained. The samples were shown to be positive for TGEV by immunofluorescence on frozen sections of the small intestine. Approximately 10 percent suspensions of the intestinal samples were prepared in 0.05M phosphate buffered saline (PBS) (pH 7.4) and clarified by centrifugation at 200×g for 10 minutes. The supernates were harvested, passed through a 0.45 $\mu$m filter (Costar, Cambridge, Mass.) and stored at −70° C. until viral isolation was attempted.

The swine testis (ST) cell line, was used to propagate and isolate TGEV field strains IA101, AR302 and the PRCV strain AR310. The ST cells were passaged and maintained as previously described by X. Zhu et al., *Am. J. Vet. Res.*, 51, 232 (1990).

Four-day-old ST cells in 25 cm² flasks (Costar, Cambridge, Mass.) were treated with Minimum Essential Medium (MEM) containing DEAE-dextran (50 μg/ml) (Sigma, St. Louis, Mo.) at 37° C. for 30 minutes before the intestinal tissue filtrate was added. Prior to inoculation onto ST cell monolayers, 0.2 ml of the intestinal filtrate was mixed with 0.8 ml of a 1:10 dilution of porcine anti-enterovirus (Group 8C) hyperimmune serum (titer of 1:1600) in MEM with 2 percent fetal bovine serum (FBS) and antibiotics (penicillin 20,000 U/ml, streptomycin 20,000 μg/ml, and amphotericin B 50 μg/ml) (GIBCO, Grand Island, N.Y.), and were incubated at 37° C. for one hour. The ST cell monolayers were inoculated with the entire 1 ml of virus and anti-enterovirus hyperimmune serum mixture and the inoculum was adsorbed onto the ST cells for 60 minutes at 37° C., after which additional MEM with 2 percent FBS plus antibiotics was added.

The cultures were incubated at 37° C. for 48 hours and observed daily for cytopathic effect. After 48 hours, whether or not CPE cytopathology was evident, all cultures were frozen and thawed three times, clarified by centrifugation at 200×g for 10 minutes, and used as inoculum for the next passage. The PRCV AR310 isolate was plaque purified a total of three times. Stock virus was then prepared from the plaque purified isolate and stored at −70° C.

The ability of the PRCV AR310 isolate to be neutralized by monoclonal antibodies or by swine polyclonal anti-TGEV hyperimmune serum was determined by a plaque reduction assay as described previously by X. Zhu et al., *Am. J. Vet. Res.*, 51, 232 (1990).

The isolate AR310 was readily neutralized by anti-TGEV hyperimmune swine serum and was also readily neutralized by anti-TGEV S glycoprotein monoclonal antibodies (Table 1).

TABLE 1

Neutralization of PRCV AR310 and TGEV by anti-Miller TGEV polyclonal and monoclonal antibodies

| Virus | Polyclonal 0024 | Monoclonal MH11 | MA5 | MA4 |
|---|---|---|---|---|
| PRCV AR310 | 1600 | 6400 | 1600 | 1600 |
| Miller TGEV | 3200 | 51200 | 25600 | 51200 |
| TGEV AR302 | 3200 | 12800 | 12800 | 12800 |
| TGEV IA101 | 1600 | 12800 | 1600 | 1600 |

*Reciprocal of the last dilution of antibodies neutralizing 80% of about 100 PFU of virus.

Radioimmunoprecipitation

A radioimmunoprecipitation (RIP) assay was utilized to determine the extent of differences in the migration of viral structural proteins of PRCV AR310. Also the Miller strain of TGEV, the TGEV field isolate AR302 (isolated from the same herd from which PRCV AR310 was isolated), the TGEV field isolate IA101, the PRCV isolate ISU-1, and mock-infected ST cells were labeled with $^{35}$S-methionine-cysteine and processed as described previously by Zhu et al., *Am. J. Vet. Res.*, 51, 232 (1990). The $M_r$ of AR310 S glycoprotein migrated at 180,000, whereas the Miller TGEV S glycoprotein migrated at 200,000.

Example 2. RNA extraction

ST cells were infected at a multiplicity of infection (moi) of 0.1 PFU/cell with plaque purified AR310. Virus was isolated from clarified cell culture supernatant fluids and was precipitated overnight at 4° C. in the presence of 7.7% polyethylene glycol and 2.3% NaCl. The precipitated virus was collected by centrifugation in a GSA rotor at 15,000 rpm for 30 minutes. The precipitated virus was suspended in 1/10th volume of TE (pH 7.4) and placed on a discontinuous sucrose (10%, 25%, and 40% in TE) gradient and centrifuged at 25,000 rpm (Beckman SW-28) for 2 hours. The virus was collected at the 25%–40% sucrose interface and was suspended in TE and then pelleted by centrifugation at 25,000 rpm (Beckman SW-28) for 45 minutes. The viral pellet was resuspended in 0.5 ml of TNE (pH 7.5) with 1% SDS and 600 μg of proteinase K and incubated at 37° C. for 30 minutes. The genomic RNA was extracted with phenol:chloroform (1:1), followed by chloroform:isoamyl alcohol (24:1), and was ethanol precipitated. The RNA was washed with 70% ethanol and dissolved in double distilled water and stored at −70° C.

Example 3. cDNA synthesis and PCR cDNA was made by AMV reverse transcriptase (RT) (Invitrogen cDNA cycle kit) using a S gene specific oligonucleotide primer for the 3' end of the S gene (5'-GGGGATCCGGACCTGTAATGACTC-GTAAG-3'') (SEQ ID NO:3). The cDNA-RNA hybrids were amplified by PCR using Taq DNA polymerase (Promega) using the following primers and cycles. The S gene was amplified with the primers (5'-GGGAATTCGGGTAAGTTGCTCATTAGAAA-3') (SEQ ID NO:4) and (5'-GGGGATCCGCAGTG-CCACGAGTCCTATCAT-3') (SEQ ID NO:5) under the following parameters: 2 cycles of 2 minutes at 94° C., 2 minutes at 48° C., and 10 minutes at 72° C.; 30 cycles of 2 minutes at 94° C., 2 minutes at 48° C., and 5 minutes at 72° C.; followed by 1 cycle of 2 minutes at 94° C., 2 minutes at 48° C., and 10 minutes at 72° C. in a DNA thermal cycler (Coy).

The PRCV AR310 S gene PCR product was separated on a 1.0% agarose gel, Genecleaned, digested with EcoR1 and BamH1 (Promega) and were directionally cloned into the pBluescript vector pKS+ (Stratagene). DNA inserts were sequenced by double-stranded DNA sequencing by the dideoxy chain termination method (Sanger et al., *PNAS USA*, 74, 5463 (1977)).

Figure 1:
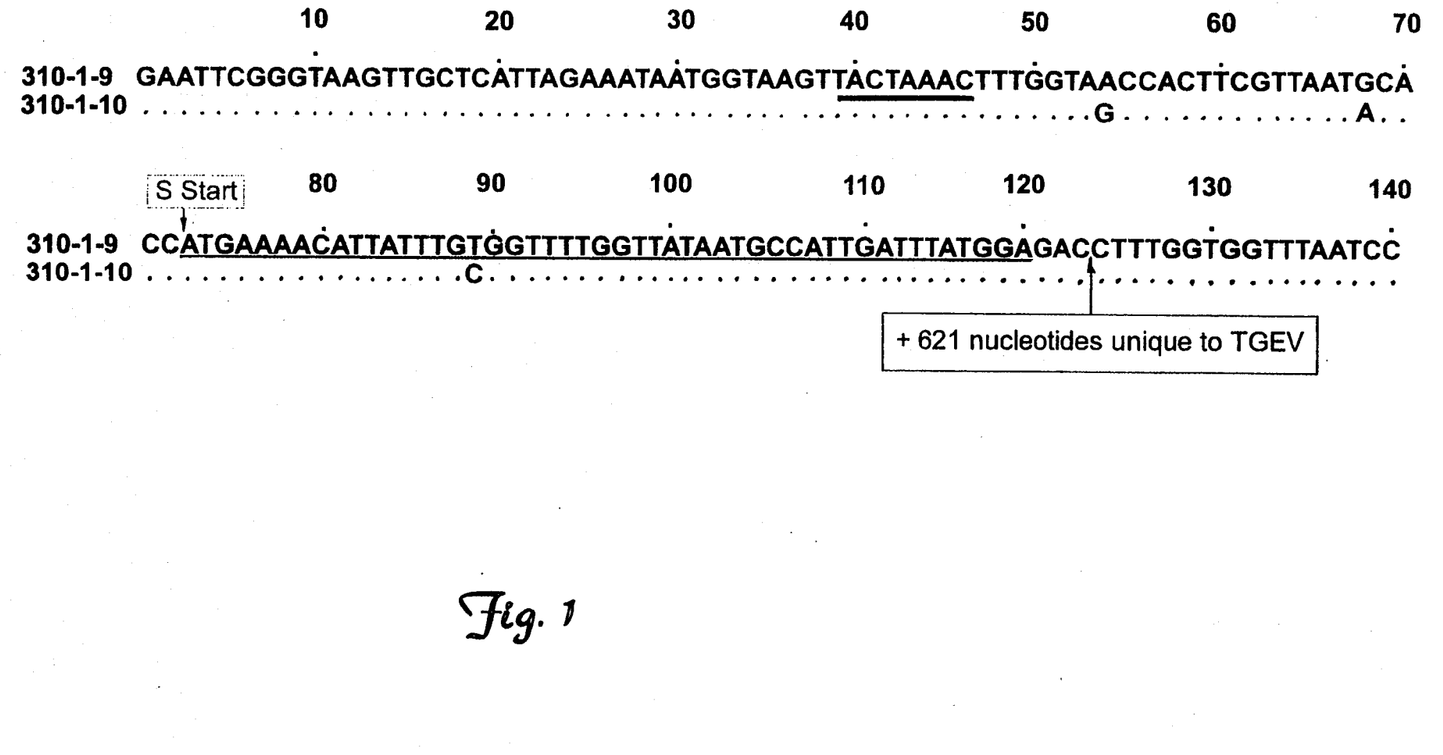
FIG. 1 compares the nucleotide sequences at the 5'-end of the S genes of two AR310 clones (SEQ ID NO:1).
Figure 2:
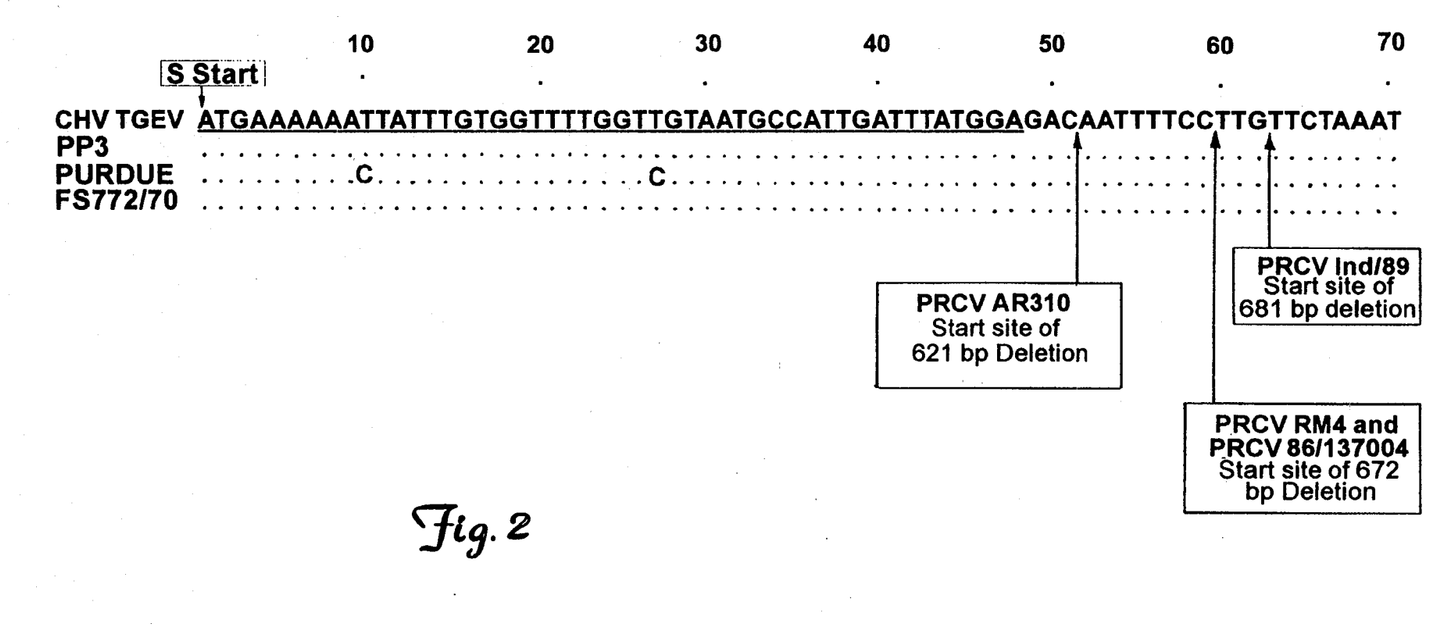
FIG. 2 compares the S gene nucleotide sequences of AR310 with three other PRCV isolates (SEQ ID NO:2).

The AR310 PCR product migrated faster than the PCR product from the virulent TGEV, indicating a deletion in the 5' end of the S gene of AR310. Two PCR clones, designated 310-1-9 and 310-1-10 were chosen for analysis. The first 140 nucleotides of these clones is shown in FIG. 1 (SEQ ID NO:1). Note the 621 bp deletion three nucleotides after the signal peptide sequence. The comparison of the S gene deletion of AR310 with those of other published PRCV isolates is shown in FIG. 2 (SEQ ID NO:1). The S gene deletion of AR310 is shorter and closer to the signal peptide region than that of the PRCV isolates RM4, PRCV 86/137004 and Ind/89.

Example 4. Replication of AR310 in gnotobiotic piglets

The sites of replication of AR310 in three-day-old gnotobiotic piglets was determined. Prior to inoculation of the gnotobiotic piglets in this study, a stock preparation of plaque purified AR310 was propagated in a gnotobiotic piglet. Five ml of MEM containing $1.0 \times 10^6$ plaque-forming units (PFU) ml of cell culture grown virus were given intranasally and orally, and two clays post inoculation (DPI) the piglet was sacrificed and the lungs and intestines were collected.

The lung tissue was used to make a 20% homogenate (w/v) in MEM and had a titer of $1 \times 10^7$ PFU/ml. No virus was isolated from the intestinal homogenate. From this pig-propagated virus stock, PRCV AR310 was diluted to contain $1.0 \times 10^6$ PFU in 5 ml in MEM. This 5 ml dose was given to four three-day-old gnotobiotic piglets intranasally (2 ml) and orally (3 ml). At 1, 2, 3, and 10 DPI, one piglet was sacrificed and tissues were collected for isolation of virus and to determine gross and microscopic lesion development. The lungs and intestines of the pigs were processed into 20% homogenates (w/v) in MEM and virus isolation was attempted on ST cell monolayers.

The site of replication of AR310 in gnotobiotic piglets was the lung tissue as shown in Table 2. Pigs A, B, and C all had AR310 present in high titer in their lungs. Pig D was the only piglet that presented both gross and microscopic lesions in lung tissue. Although lesions were present in the lungs of pig D, no virus was detectable.

TABLE 2

Virus replication and lesion development in three-day-old gnotobiotic piglets inoculated with PRCV AR310

| | Dose[a] (PFU) | DPI Necropsied | Lesions[b] Lung | Intestine | Virus Isolation[c] Lung | Intestine | Lung Titer[d] (PFU/ml) |
|---|---|---|---|---|---|---|---|
| Pig A | $1.0 \times 10^6$ | 1 | — | — | + | n/a | $2.5 \times 10^7$ |
| Pig B | $1.0 \times 10^6$ | 2 | — | — | + | n/a | $2.5 \times 10^7$ |
| Pig C | $1.0 \times 10^6$ | 3 | — | — | + | n/a | $1.0 \times 10^7$ |
| Pig D | $1.0 \times 10^6$ | 10 | + | — | — | n/a | ND |

[a]Total PFU in 5 ml of MEM given orally (3 ml) and intranasally (2 ml).
[b]Gross and microscopically.
[c]Isolation of virus from 20% lung or intestinal homogenates.
[d]Virus titers from 20% lung homogenates.

Example 5. Experimental Reproduction of Pneumonia in Gnotobiotic Pigs Using AR310

A. Virus Stock. PRCV AR310 was isolated from homogenates of intestinal tracts by inoculation of swine testis (ST) cell line as described in Example 1. Virus was plaque purified three times and gnotobiotic pigs were inoculated oronasally at the 10th cell culture passage. Lungs from a gnotobiotic pig at three days after infection were homogenized, clarified, and filtered through 0.22 μm and served as virus stock for this experiment. The lung filtrate virus stock had a titer of $1\times10^7$ PFU/ml.

B. Gnotobiotic pigs. Gnotobiotic pigs were obtained by closed hysterectomy and maintained in gnotobiotic isolators as previously described by O. P. Miniats et al., *Can. J. Comp. Med.*, 42, 428 (1978). The isolators were maintained at an ambient temperature of 30° C. and pigs were fed commercial milk substitute. Fecal swabs were collected from each pig at the time of necropsy prior to removal from the isolators to check bacterial sterility.

C. Experimental transmission. Sixteen gnotobiotic pigs were randomly divided into four isolators containing four pigs each. Eight pigs served as mock-infected controls. Eight pigs were challenged intranasally with 3 ml and orally with 1 ml containing a total of $2\times10^6$ PFU of AR310. Intranasal inoculations were made by slowly dripping the material into the nares and oral inoculations by injecting the material into the back of the mouth. The pigs were monitored for signs of enteric and respiratory disease. Two control pigs and two PRCV AR310 inoculated pigs were euthanized by electrocution 3, 5, 10 and 15 DPI. Nasal and rectal swabs were collected daily from each pig. Virus isolation was attempted from the lungs, intestines, nasal and rectal swabs.

D. Virus isolation and titration from experimental pigs. Lungs or small intestines were homogenized in Eagle's minimal essential medium (20% w/v), clarified at $1000\times g$ for 10 minutes and filtered through 0.22 μm. Confluent 3–5 day old monolayers of ST cells in 25 $cm^2$ flasks were inoculated with 0.2 ml of filtrate. After one hour incubation at 37° C., the monolayer was washed and new culture medium was added. Cells were observed for cytopathic effect. If no cytopathic effect was observed, the cells in the flasks were frozen and thawed three times and cell lysates inoculated onto new monolayers. Samples were passed three times. The presence of PRCV was confirmed by indirect immunofluorescence using gnotobiotic pig antisera to the Miller strain of TGEV and mouse anti-TGEV-S monoclonal antibodies as disclosed by X. Zhu et al., *Am. J. Vet. Res.*, 51, 232 (1990). Virus titration was performed by inoculation of ST monolayers with 10-fold concentrations of tissue filtrates.

E. Microscopic examination. Brain, nasal turbinate, heart, lung, duodenum, jejunum, ileum, colon, liver and kidney of all pigs were collected in 10 percent neutral buffered formalin, embedded in paraffin,, sectioned at 4 microns, and stained with hematoxylin and eosin (HE). Lungs were inflated with formalin at the time of necropsy by injection into the trachea until full inflation was achieved and then the trachea was tied off and the entire lung submerged. Histologic lesions were evaluated by light microscopy.

F. Results.

1. Experimental reproduction of lesions. All control and PRCV-inoculated pigs remained clinically normal throughout the experiment. The pigs' appetites remained good and no significant elevations in body temperatures were seen.

At 3 days post-infection (DPI), one of two PRCV-infected pigs had gross pneumonic lesions characterized by 20% multifocal-to-coalescing reddish-tan consolidation of the lung involving parts of all lobes. Both PRCV-infected pigs killed at 5 DPI had gross lesions similar to those at 3 DPI but with more interlobular edema present. At 10 DPI, there was bilateral multifocal reddish-tan consolidation of 60% of the lungs of both pigs. At 15 DPI, there were no visible gross lesions in the infected pigs. There were no gross lesions in control pigs.

Microscopically, interstitial septa were mildly thickened with mixed mononuclear cells. There was moderate lymphoplasmacytic and histiocytic brochiolar and alveolar exudation, and mild multifocal type II pneumocyte hyper-trophy and proliferation. There was also moderate to severe airway epithelial necrosis, squamous metaplasia, dysplasia and proliferation involving all sizes of airways. The pulmonary lesions were mild by 3 DPI, moderate by 5 DPI, severe by 10 DPI and nearly resolved by 15 DPI. No lesions were detected in nasal turbinates. Microscopic lesions were not visible in the small or large intestines of the infected pigs. There were no microscopic lesions in lungs or intestines of control pigs.

2. Virus isolation from experimental pigs. PRCV was not detected in the small intestines of any of the pigs. PRCV was isolated from the lungs of two PRCV-inoculated pigs at 5 DPI. Virus was also detected in the nasal swabs at 3 and 4 DPI and rectal swabs at 1 and 2 DPI. PRCV was not detected in any of the control pigs.

G. Discussion. This invention provides a pneumopathogenic strain of PRCV isolated in the United States. PRCV AR310 was isolated from the intestines of a nursery pig from a herd with an endemic TGE problem. Plaque purified PRCV AR310 caused moderate bronchointerstitial pneumonia following oronasal inoculation. No significant clinical respiratory disease was seen in the gnotobiotic pigs, probably because of the gnotobiotic environment and its absence of other microorganisms. It would be expected that the lesions caused by PRCV AR310 as demonstrated in this study would seriously predispose conventional pigs to subsequent secondary bacterial infections and clinical respiratory disease.

All publications and patents are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed is:

1. A vaccine effective to prevent pathogenic porcine respiratory coronavirus (PRCV) infection or porcine transmissible gastroenteritis virus (TGEV) infection, comprising an inactivated or attenuated biologically pure culture of PRCV ATCC 2384, in combination with a physiologically acceptable carrier.

2. The vaccine of claim 1 wherein the physiologically acceptable carrier is a liquid.

3. The vaccine of claim 1 which also comprises an effective amount of an immunological adjuvant.

4. A method of immunizing swine against PRCV which comprises administering to swine an immunologically effective amount of the vaccine of claim 1.

5. A method of immunizing swine against TGEV which comprises administering to swine an immunologically effective amount of the vaccine of claim 1.

6. A biologically pure culture of pathogenic porcine respiratory coronavirus (PRCV) ATCC VR 2384.

* * * * *

UNITED STATES PATENT AND TRADEMARK OFFICE
CERTIFICATE OF CORRECTION

PATENT NO. :  5,419,907

DATED :  May 30, 1995

INVENTOR(S) :  Prem S. Paul et al.

It is certified that error appears in the above-identified patent and that said Letters Patent is hereby corrected as shown below:

At Col. 13, line 41, claim 1, please delete "ATCC 2384," and insert --ATCC VR 2384,--.

Signed and Sealed this

Fifteenth Day of December, 1998

Attest:

BRUCE LEHMAN

Attesting Officer

Commissioner of Patents and Trademarks